United States Patent [19]

Iwaya et al.

[11] Patent Number: 5,667,722
[45] Date of Patent: Sep. 16, 1997

[54] ANTIFERROELECTRIC LIQUID CRYSTAL COMPOUND AND ANTIFERROELECTRIC LIQUID CRYSTAL COMPOSITION CONTAINING THE SAME

[75] Inventors: Yukiharu Iwaya; Mamoru Yamada; Hitoshi Kondo; Toshimitsu Hagiwara, all of Kanagawa, Japan

[73] Assignee: Takasago International Corporation, Tokyo, Japan

[21] Appl. No.: 653,744

[22] Filed: May 23, 1996

[30] Foreign Application Priority Data

May 29, 1995 [JP] Japan .................. 7-152753

[51] Int. Cl.[6] .................. C09K 19/34; C07D 239/02
[52] U.S. Cl. .................. 252/299.61; 544/299; 544/315; 544/318
[58] Field of Search .................. 252/299.01, 299.61; 544/299, 315, 318

[56] References Cited

U.S. PATENT DOCUMENTS

| 5,316,694 | 5/1994 | Murashiro | 252/299.61 |
| 5,378,392 | 1/1995 | Murashiro | 252/299.01 |
| 5,405,553 | 4/1995 | Terada et al. | 252/299.61 |
| 5,413,735 | 5/1995 | Yamashita et al. | 252/299.61 |

*Primary Examiner*—Shean C. Wu
*Attorney, Agent, or Firm*—Sughrue, Mion, Zinn, Macpeak, and Seas

[57] ABSTRACT

An antiferroelectric liquid crystal compound represented by the following general formula (I):

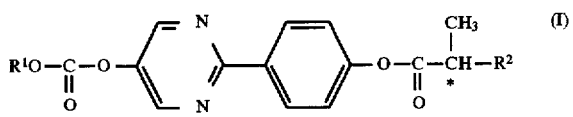

wherein $R^1$ represents an alkyl group having 6 to 16 carbon atoms; $R^2$ represents a straight chain alkyl group having 3 to 8 carbon atoms or a branched alkyl group having 4 to 10 carbon atoms; and * means an asymmetric carbon atom, and an antiferroelectric liquid crystal composition comprising at least one liquid crystal compound as defined above. The optically active compound of the present invention is highly miscible with a number of known antiferroelectric liquid crystal compounds and thus capable of providing liquid crystal materials having improved temperature properties. A liquid crystal composition containing the optically active compound of the present invention is applicable to electro-optical devices with the use of antiferroelectric liquid crystals.

8 Claims, No Drawings

ANTIFERROELECTRIC LIQUID CRYSTAL COMPOUND AND ANTIFERROELECTRIC LIQUID CRYSTAL COMPOSITION CONTAINING THE SAME

FIELD OF THE INVENTION

This invention relates to a novel antiferroelectric liquid crystal compound which is useful as an antiferroelectric liquid crystal material to be used in liquid crystal electro-optical devices. It also relates to an antiferroelectric liquid crystal composition containing this compound.

BACKGROUND OF THE INVENTION

Liquid crystal display devices have been used in various products including watches and electronic calculators, since they are thin and light and consume less electricity. The twisted nematic (TN) display system with the use of nematic liquid crystals is adopted in liquid crystal display devices commonly employed today. Among driving systems for liquid crystal display devices, the simple matrix system, whereby the liquid crystal display device is driven only by electrodes provided on upper and lower substrates, is the most suitable one from the viewpoints of productivity and cost. However, nematic liquid crystals have a slow response time and provide a reduction of the contrast with an increase in the display density, which makes it difficult to construct a high-density display thereby. Accordingly, a very expensive driving system called the active matrix system, wherein each pixel is provided with a thin film transistor (TFT), has been employed in the displays of computers, etc. The production of these displays requires many steps and thus costs a great deal. Thus attempts have been made to cut down the production cost thereof.

On the other hand, Meyer et al. synthesized 2-methylbutyl 4-(n-decyloxybenzylideneamino)cinnamate showing a ferroelectric liquid crystal phase (Sc* phase) in 1975 [R. B. Meyer et al., *J. Phys. (France)*, 36, L69 (1975)]. Further, Clark et al. proposed a surface stabilized ferroelectric liquid crystal device [N. A. Clark et al., *Appl. Phys. Lett.*, 36, 899 (1980)]. Under these circumstances, it is expected that a liquid crystal display device having a fast switching time and an excellent bistability will be produced. Thus a number of ferroelectric liquid crystal materials have been synthesized and proposed so far.

However, the alignment state is much more complicated than expected. Thus, the direction of liquid crystal molecules in a layer is liable to be twisted, which makes it impossible to obtain a high contrast ratio. In addition, it was anticipated that the layer stood perpendicularly to the upper and lower substrates (i.e., a bookshelf structure). In practice, however, the layer is folded (i.e., a chevron structure) and, as a result, zigzag defects arise, which also reduce the contrast ratio. Furthermore, there arises another problem of spontaneous polarization characteristic to ferroelectric liquid crystals. Namely, it has been found that when a memory state is kept for a long period of time, the inversion hardly occurs even under the application of the reverse electrical field (this phenomenon will be hereinafter referred to as ghost effect), thus reducing the contrast.

Recently, there has been reported the existence of a liquid crystal phase by which these problems encountered in ferroelectric liquid crystals might be solved. This liquid crystal phase is an antiferroelectric liquid crystal phase (ScA* phase) having a third stable state in addition to the two stable states (bistability) of the ferroelectric liquid crystal phase. In this third stable state, the molecular tilt direction is reversed between two adjacent layers and thus the spontaneous polarization is drowned out. Although this ScA* phase appears on the lower temperature side of the Sc* phase, the switching time of this ScA* phase is almost comparable to that of the Sc* phase. Moreover, the chevron structure can be switched to the bookshelf structure by changing the applied electrical field. In the ScA* phase, therefore, the bookshelf structure can be easily established by applying an appropriate electric field and thus defects can be eliminated. Further, polarizers and analyzers are provided in such a manner as to make the third state (i.e., the stable state under the application of no voltage) dark and the two ferroelectric states are switched to each other by applying an alternating electric field. Accordingly, no such ghost effect as observed in ferroelectric liquid crystal devices occurs in this case.

In addition, an antiferroelectric liquid crystal phase is also observed in the smectic I phase corresponding to a tilted smectic B phase. Because of being a phase of higher order, it has a low response speed. Thus, the ScA* phase of a low viscosity alone might be applicable to a high contrast display. An antiferroelectric liquid crystal device with the use of this ScA* phase enables simple matrix driving at a low cost and a high productivity. It is said that a display device with a high contrast ratio can be easily achieved thereby.

The antiferroelectric liquid crystal phase was found for the first time in 4-(1-methylheptyloxycarbonyl)phenyl-4'-octyloxybiphenyl-4-carboxylate (hereinafter referred to simply as MHPOBC) represented by the following chemical formula [Chandani et al., *Jpn. J. Appl. Phys.*, 27, L729 (1988)]:

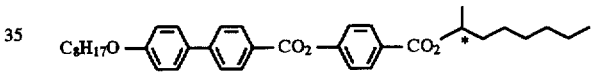

Subsequently, it was clarified that the ScA* phase also appeared when a 1-methylheptyl group in the chiral site was replaced by a 1-trifluoromethylheptyl group. The compound prepared by introducing this 1-trifluoromethylheptyl group exhibits the antiferroelectric liquid crystal phase in a relatively stable state. Accordingly, many derivatives thereof have been reported hitherto as compounds showing the ScA* phase.

In the prior art, a chiral nematic liquid crystal composition or a ferroelectric liquid crystal composition are obtained by adding an optically active compound respectively to a nematic liquid crystal composition or a smectic C liquid crystal composition free from any optically active compound. In the case of an antiferroelectric liquid crystal composition, on the other hand, there have been found few compounds being free from any optically active group and having the same layer structure as that of antiferroelectric liquid crystal phases. Accordingly, an antiferroelectric liquid crystal composition is obtained by constructing a composition of a compound showing an antiferroelectric liquid crystal phase and adding a smectic C liquid crystal compound thereto in such a manner as not to break the layer structure thereof [in general, in an amount of from 30 to 40% (by weight, the same will apply hereinafter)].

However, there have been found few liquid crystal compounds with two rings showing an antiferroelectric phase. That is to say, there has been known no such compound except a cinnamate derivative represented by the following chemical formula, so long as the present inventors know

[Proceedings of 18th Liquid Crystal Conference in Niigata, Japan, (1992) 3B419].

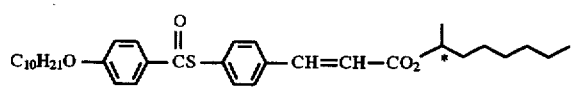

As a compound formally including the liquid crystal compound of the present invention represented by the general formula (I) as will be described hereinafter, JP-A-3-12476 (the term "JP-A" as used herein means an "unexamined published Japanese patent application") discloses a phenylpyrimidine derivative represented by the following general formula (II):

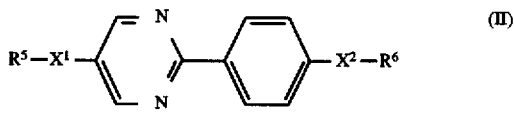

wherein $R^5$ and $R^6$ each represent a straight chain or branched alkyl group having 1 to 18 carbon atoms which can be optionally substituted, provided that at least one of them is an optically active one; $X^1$ represents —O—, —OC(=O)—, —C(=O)O—, or —OC(=O)O—; and $X^2$ represents a single bond, —O—, —OC(=O)—, —C(=O)O—, or —OC(=O)O—.

However, the liquid crystal compound disclosed in the above-mentioned patent is not an antiferroelectric liquid crystal compound but a compound which is employed in a ferroelectric chiral smectic liquid crystal composition.

Further, JP-A-4-213387 discloses a phenylpyrimidine derivative represented by the following general formula (III):

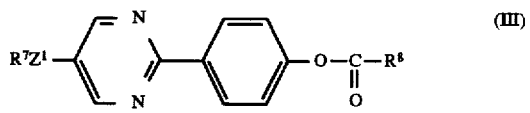

wherein $R^7$ and $R^8$ each represent a straight chain or branched alkyl group having 1 to 18 carbon atoms optionally substituted by an alkoxy group having 1 to 12 carbon atoms, provided that $R^7$ and $R^8$ are both optically inactive ones; and $Z^1$ represents a single bond, —O—, —OC(=O)—, —C(=O)O—, or —OC(=O)O—.

However, this derivative is not an antiferroelectric liquid crystal compound but a compound which shows the smectic C phase and is to be used in a ferroelectric liquid crystal device, similar to the one described above.

When the 1-methylheptyl group in the chiral site of the above-mentioned MHPOBC is replaced by a 1-methylhexyl group, the ferroelectric liquid crystal phase appears alone without showing the ScA* phase. When a 2-methylalkyl group is used, the ferroelectric phase alone appears but no ScA* phase is observed. That is to say, it is highly difficult to structurally modify the chiral site. Although the molecular modification of the chiral site has been discussed, no antiferroelectric liquid crystal phase can be hardly achieved.

There have been generally synthesized various compounds modified in the liquid crystal core side, in particular, the ring structure. Similar to the conventional nematic liquid crystals, antiferroelectric liquid crystals should satisfy various requirements for practical use. These requirements can be hardly satisfied by using a single compound or a group of analogous compounds as described above. Namely, it is required to use a number of compounds differing in properties.

The above-mentioned cinnamate derivative, which is the only compound known as antiferroelectric liquid crystals with two rings, cannot be added to a liquid crystal composition to be used in a liquid crystal display, since it is poor in stability to light. Accordingly, chemically and optically stable two-ring antiferroelectric liquid crystal compounds have never been reported as far as the inventors know. However, in order to obtain a liquid crystal composition having a lower viscosity and a broader temperature range, it is necessary to add a two-ring compound to the composition.

In view of the above, a method of adding a two-ring liquid crystal compound showing a smectic C phase, in which the liquid crystal molecule is tilted in the layer as in the antiferroelectric liquid crystal phase, to the antiferroelectric liquid crystal composition to improve the temperature range and viscosity has been proposed. In this case, however, the antiferroelectric liquid crystal phase would disappear unless a three-ring antiferroelectric liquid crystal compound having higher viscosity such as MHPOBC is added to the composition in an amount of 60 % or more. Accordingly, even in this method, it has been difficult to obtain the desired effects, i.e., broadening the temperature range, lowering the viscosity, etc.

Under these circumstances, it has been urgently required to develop a two-ring compound which is a liquid crystal compound showing chemically and optically stable antiferroelectricity and capable of maintaining the antiferroelectric liquid crystal phase even though added in a large amount to a composition thereof.

Accordingly, the present invention aims at providing a novel optically active compound, which shows an antiferroelectric liquid crystal phase or is highly miscible with known compounds showing an antiferroelectric liquid crystal phase, thus being capable of broadening the temperature range of the antiferroelectric phase, and an antiferroelectric liquid crystal composition containing this optically active compound.

The present inventors have conducted extensive studies on optically active compounds being highly miscible with known compounds showing an antiferroelectric liquid crystal phase and thus capable of broadening the temperature range of the antiferroelectric phase.

In the process of these studies, it has been clarified that the compound disclosed in the above-mentioned JP-A-3-12476, which is one known as showing a ferroelectric chiral smectic C phase or merely a smectic C phase, is unusable as a compound capable of achieving a stable antiferroelectric liquid crystal phase when added to an antiferroelectric liquid crystal compound or an antiferroelectric liquid crystal composition at a ratio of 40% or above. When this compound is added to an antiferroelectric liquid crystal compound or a composition thereof at a ratio of 40% or above, the obtained mixture becomes a smectic A phase liquid crystal composition or a ferroelectric liquid crystal composition as described in the Comparative Examples herein. This is seemingly because the ferroelectric liquid crystal phase would differ from the antiferroelectric liquid crystal phase in layer structure. When ferroelectric liquid crystals or an optically inactive smectic C liquid crystal compound is added at a ratio of 40% or above to a compound showing an antiferroelectric liquid crystal phase, therefore, the layer structure of the antiferroelectric liquid crystal phase would fall into disorder.

Regarding the compound described in JP-A-4-213387, this patent document states nothing about the phase sequence, phase transition temperature, etc., thereof. This compound, which is optically inactive as described in the claims, is one to be used in a ferroelectric liquid crystal device and thus seemingly shows a smectic C phase. Accordingly, it is considered that this compound is also unusable as a compound capable of achieving a stable antiferroelectric liquid crystal phase when added at a ratio of 40% or above to an antiferroelectric liquid crystal compound or an antiferroelectric liquid crystal composition.

Thus, the present inventors synthesized the following compound which is the only one concretely disclosed in the detailed description of the specification of the above-mentioned patent:

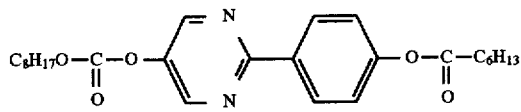

and examined the phase transition thereof (Comparative Example 7). As a result, it is proved that this compound shows nematic and smectic C phases but not an antiferroelectric liquid crystal phase. It is also found that when this compound is added in an amount of 49.3% by weight to a known compound showing an antiferroelectric liquid crystal phase, the resulting mixture is a liquid crystal composition showing a smectic A phase alone.

On the basis of this discussion, the present inventors have conducted extensive and detailed studies on bicyclic compounds showing an antiferroelectric liquid crystal phase. During these studies, they have successfully found that the compound of the present invention represented by the general formula (I) as will be given hereinbelow, which is an optically active 2-methylalkanoic acid derivative having an alkyl chain of a length falling within a definite range and a carbonate bond, shows an antiferroelectric liquid crystal phase, is highly miscible with known compounds showing an antiferroelectric liquid crystal phase, and exhibits a stable antiferroelectric liquid crystal phase on mixing, thus broadening the temperature range of the antiferroelectric phase in particular toward the lower temperature side. They have furthermore found that the compound represented by the general formula (I) shows either a monotropic antiferroelectric liquid crystal phase or no liquid crystal phase when used alone but provides an antiferroelectric liquid crystal composition when added at a ratio of 60% or above to an antiferroelectric liquid crystal compound or an optically inactive smectic C liquid crystal compound. The present invention has been completed based on these findings. That is to say, the present inventors have found that the compound represented by the general formula (I) has an antiferroelectric liquid crystal phase at around its crystallization temperature (in the process of lowering temperature) or below.

SUMMARY OF THE INVENTION

Accordingly, the present invention is as follows.

1. An antiferroelectric liquid crystal compound represented by the following general formula (I):

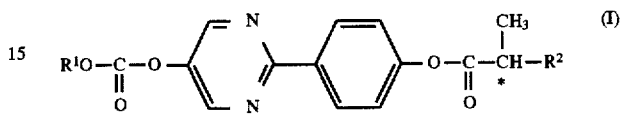

wherein $R^1$ represents an alkyl group having 6 to 16 carbon atoms; $R^2$ represents a straight chain alkyl group having 3 to 8 carbon atoms or a branched alkyl group having 4 to 10 carbon atoms; and * means an asymmetric carbon atom.

2. An antiferroelectric liquid crystal composition comprising at least one antiferroelectric liquid crystal compound represented by the above general formula (I).

DETAILED DESCRIPTION OF THE INVENTION

In the compound of the present invention represented by the general formula (I), which is specified by the above-mentioned carbonate, optically active 2-methylalkanate, the direction of the phenylpyrimidine ring, etc., the alkyl group $R^1$ may be either a straight chain or branched one. However, a straight chain alkyl group is preferable and one having 6 to 12 carbon atoms is still more preferable therefor. The alkyl group $R^2$ may be either a straight chain alkyl group having 3 to 8 carbon atoms or a branched one having 4 to 10 carbon atoms. In any case, an alkyl group having 3 to 6 carbon atoms in the linear chain is preferable therefor from the viewpoints of the stability of the antiferroelectric liquid crystal phase, melting point and viscosity.

Preferable examples of the compound of the present invention represented by the general formula (I) include the following ones.

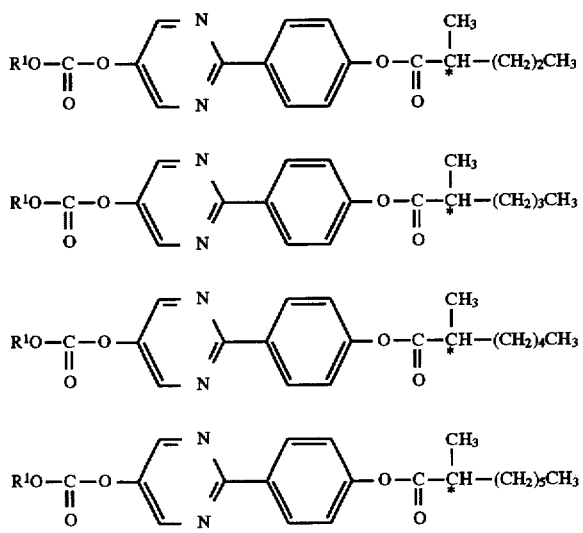

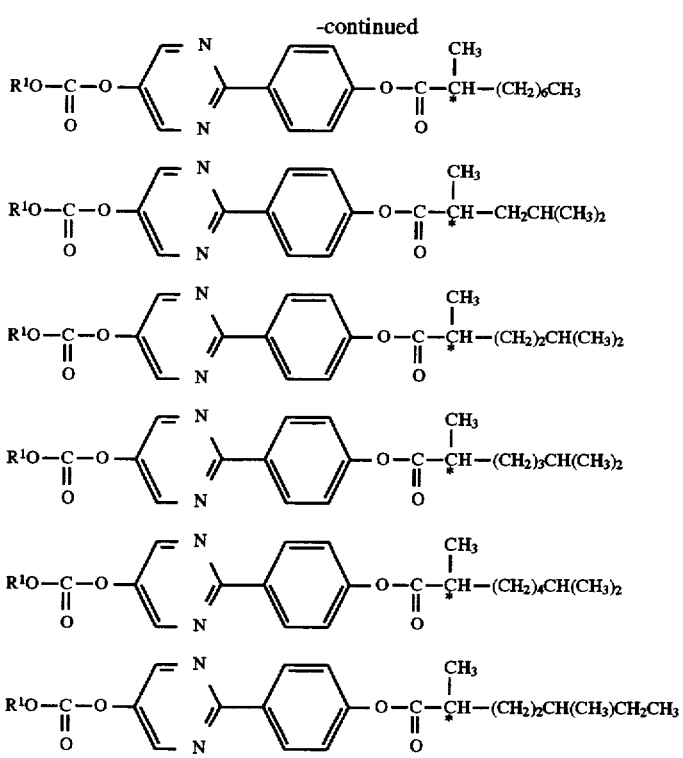

In these compounds, $R^1$ in the formula represents an alkyl group having 6 to 16 carbon atoms. Although it may be a branched one, a straight chain alkyl group is preferable therefor.

The liquid crystal compound of the present invention represented by the general formula (I) can be synthesized in, for example, the following manner. Namely, an optically active 2-methylalkanoic acid prepared as described below is converted into a carboxylic acid halide in accordance with a conventional method. Then this product is reacted with the following phenol derivative (IV), which has been synthesized by a conventional method, in the presence of pyridine to thereby give the target compound.

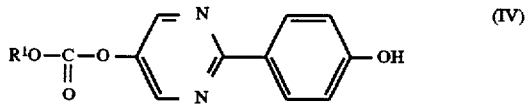

(IV)

The optically active 2-methylalkanoic acid as described above can be obtained by, for example, asymmetrically hydrogenating the corresponding 2-methyl-2-alkenoic acid or optically resolving a racemic 2-methylalkanoic acid or a derivative thereof by using lipase.

The above-mentioned phenol derivative (IV) can be obtained by, for example, the following synthesis method wherein Bz represents a benzyl group.

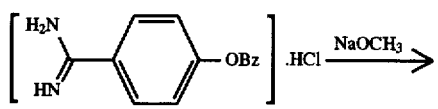

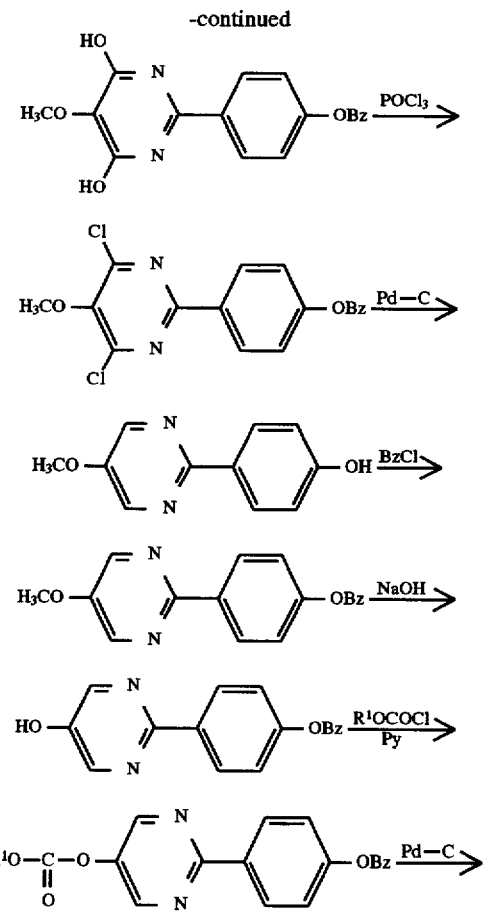

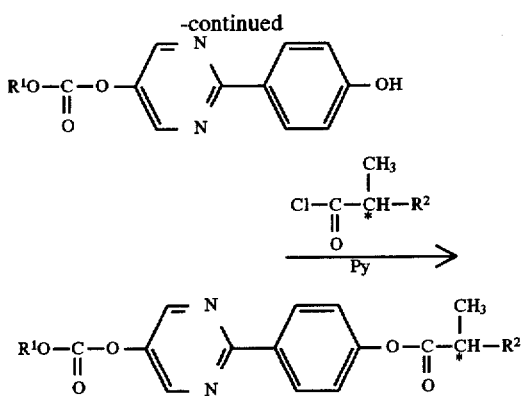

Namely, the synthesis to 2-(4-benzyloxyphenyl)-5-hydroxypyrimidine may be performed in accordance with a conventional manner described in, for example, U.S. Pat. No. 5,290,477. The 5-hydroxypyrimidine derivative thus obtained is reacted with an alkyl chloroformate in the presence of pyridine to thereby give a carbonate derivative. The obtained product is then hydrogenated by using palladium/carbon under atmospheric pressure to eliminate the benzyl group. Thus the phenol derivative (IV) can be obtained.

Many of the compounds of the present invention represented by the general formula (I) show an antiferroelectric liquid crystal phase by themselves. Although some of these compounds show no liquid crystal phase, they are highly miscible with known antiferroelectric liquid crystal compounds. Therefore, antiferroelectric liquid crystal compositions can be easily obtained by mixing the compound (I) with the known ones. Preferable examples of the antiferroelectric liquid crystal compounds include those represented by the following general formulae.

chiral smectic C phase (for example, phenylpyrimidine, phenyl benzoate). It is therefore possible to obtain antiferroelectric liquid crystal compositions by mixing the compound of the general formula (I) with compounds showing a smectic C phase or a chiral smectic C phase within such a range as being capable of maintaining the layer structure of the antiferroelectric liquid crystal phase.

When an antiferroelectric liquid crystal composition is prepared by mixing the antiferroelectric liquid crystal compound of the present invention with a known antiferroelectric liquid crystal compound, it is preferable to add the liquid crystal compound of the present invention in an amount of from 1 to 60% by weight, still more preferably from 20 to 60% by weight. When the antiferroelectric liquid crystal composition thus obtained is further mixed with a ferroelectric liquid crystal compound or an optically inactive smectic C liquid crystal compound to thereby give an antiferroelectric liquid crystal composition, it is important that the ferroelectric liquid crystal compound or the optically inactive smectic C liquid crystal compound is employed in an amount of not more than 40% by weight based on the antiferroelectric liquid crystal composition mixture.

When the compound of the present invention is mixed with a ferroelectric liquid crystal compound to thereby give an antiferroelectric liquid crystal composition, it is important that the resulting composition contains at least 60% by weight of the compound of the present invention.

As described above, the liquid crystal compound of the present invention is highly miscible with conventionally known compounds showing a highly stable antiferroelectric liquid crystal phase and, therefore, can broaden the temperature range of the antiferroelectric phase. Thus the compound of the present invention is highly useful as a material to be used in an electro-optical device with the use of antiferroelectric liquid crystals.

To further illustrate the present invention in greater detail, and not by way of limitation, the following Examples will be given.

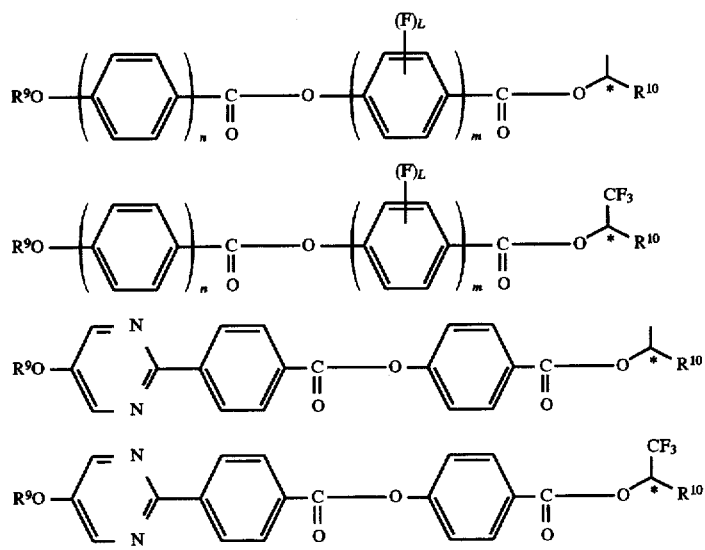

In these formulae, n and m each represent an integer of 1 or 2, provided that n+m=3, l represents 0 or 1, and $R^9$ and $R^{10}$ each represent a straight chain alkyl group.

The liquid crystal compound of the present invention represented by the general formula (I) is also highly miscible with known compounds showing a smectic C phase or a In these Examples, phase transition points were determined by observing under a polarizing microscope and measuring with the use of a differential scanning calorimeter (DSC). An antiferroelectric liquid crystal phase was identified by a so-called miscibility test and a contact method. In these examples, all percentages are by weight except those showing yields.

EXAMPLE 1

Synthesis of 2-(4-(S)-2-methyloctanoyloxyphenyl)-5-decyloxycarbonyloxy-1,3-pyrimidine:

(1) Synthesis of 2-(4-benzyloxyphenyl)-5-decyloxycarbonyloxy-1,3-pyrimidine:

To a three-necked flask (200 ml) were added under a nitrogen gas stream 4.2 g (12.0 mmol) of 2-(4-benzyloxyphenyl)-5-hydroxy-1,3-pyrimidine, 1.64 g (20.8 mmol) of pyridine and 70 ml of dichloromethane. Then 3.44 g (15.6 mmol) of decyl chloroformate was dropped thereinto at 0° C. After the completion of the addition, the resulting mixture was stirred at room temperature for 17 hours. After the completion of the reaction, the reaction mixture was washed successively with 5% hydrochloric acid and water and dried over anhydrous magnesium sulfate. After drying and distilling off the solvent, the obtained residue was recrystallized from ethyl acetate and methanol. Thus 5.00 g of the target compound was obtained. Yield: 90%.

(2) Synthesis of 2-(4-hydroxyphenyl)-5-decyloxycarbonyloxy-1,3-pyrimidine:

To a three-necked flask (200 ml) were added 5.00 g (10.8 mmol) of 2-(4-benzyloxyphenyl)-5-decyloxycarbonyloxy-1,3-pyrimidine, 80 ml of THF and 0.50 g of palladium/carbon followed by hydrogenation under 1 atm for 22 hours. After the completion of the reaction, the palladium/carbon was filtered off and the solvent was distilled off. Thus 4.00 g of the target compound was obtained. Yield: 99%.

(3) Synthesis of 2-(4-(S)-2-methyloctanoyloxyphenyl)-5-decyloxycarbonyloxy-1,3-pyrimidine:

To a three-necked flask (50 ml) were added under a nitrogen gas stream 7.07 g (80.25 mmol) of thionyl chloride and 2.54 g (16.05 mmol) of (S)-2-methyloctanoic acid. The resulting mixture was reacted at 80 ° C for 3 hours. After the completion of the reaction, the excessive thionyl chloride was distilled off to thereby give an acid chloride to be used in the subsequent reaction. Separately, to a three-necked flask (200 ml) were added 4.00 g (10.7 mmol) of 2-(4-hydroxyphenyl)-5-decyloxycarbonyloxy-1,3-pyrimidine, 80 ml of dichloromethane and 2.54 g (32.1 mmol) of pyridine. Then the acid chloride prepared above was dropped thereinto at 0° C. After the completion of the addition, the resulting mixture was stirred at room temperature for 2 hours. After the completion of the reaction, the mixture was washed with 5% hydrochloric acid followed by separation. The organic layer thus obtained was washed successively with a saturated aqueous solution of sodium hydrogencarbonate and water and dried over anhydrous magnesium sulfate. After drying and distilling off the solvent, the residue was purified by silica gel column chromatography (toluene/ethyl acetate=10/1, by volume) and purified by using an ODS column. Thus 3.21 g of the target compound was obtained. Yield: 58.7%.

1H-NMR (CDCl$_3$) ppm: 0.89 (6H, m), 1.33 (25H, m), 1.59 (1H, m), 1.78 (3H, m), 2.71 (1H, m), 4.31 (2H, t), 7.20 (2H, d, J=8.8 Hz), 8.45 (2H, d, J=8.8 Hz), 8.721 (2H, s). MS (m/e): 513 (M+, +H).

This compound melted at 60° C. to give an isotropic liquid phase. When cooled, it monotropically showed a tilted smectic phase. The transition point from this phase into the isotropic liquid phase was 45° C. The results of a contact test and a miscibility test with 4-(1-methylheptyloxycarbonyl) phenyl-4'-decyloxybiphenyl-4-carboxylate (hereinafter referred to simply as MHPDBC), i.e., a known compound showing an antiferroelectric liquid crystal phase, indicated that the liquid crystal phase observed herein was an antiferroelectric liquid crystal phase.

EXAMPLE 2

Synthesis of 2-(4-(S)-2,6-dimethylheptanoyloxyphenyl)-5-decyloxycarbonyloxy-1,3-pyrimidine:

Synthesis was performed in the same manner as the one of Example 1 but using (S)-2,6-dimethylheptanoic acid as a substitute for the (S)-2-methyloctanoic acid employed in Example 1 (3).

1H-NMR (CDCl$_3$) ppm: 0.89 (9H, m), 1.28 (17H, m), 1.42 (4H, m), 1.57 (2H, m), 1.76 (3H, m), 2.71 (1H, m), 4.31 (2H, t), 7.19 (2H, d, J=8.8 Hz), 8.45 (2H, d, J=8.9 Hz), 8.71 (2H, s).

MS (m/e): 512 (M+).

This compound melted at 64.5° C. to give an isotropic liquid phase. When cooled quickly, it showed a tilted smectic liquid crystal phase immediately before crystallization. Then it was added in an amount of 56% by weight to MHPDBC known as antiferroelectric liquid crystals and the phase transition points were observed. As a result, a mixture of an isotropic liquid with a smectic A phase was observed from the higher temperature side. At 57° C., the whole mixture underwent transition to the antiferroelectric liquid crystal phase. The results of a contact test of this compound with the compound of Example 1 indicated that the tilted smectic phases were the same, i.e., the antiferroelectric liquid crystal phase.

EXAMPLE 3

Synthesis of 2-(4-(S)-2,6-dimethylheptanoyloxyphenyl)-5-hexyloxycarbonyloxy-1,3-pyrimidine:

Synthesis was performed in the same manner as the one of Example 2 but using hexyl chloroformate as a substitute for the decyl chloroformate employed in Example 1 (1).

1H-NMR (CDCl$_3$) ppm: 0.90 (9H, m), 1.32 (9H, m), 1.43 (4H, m), 1.57 (2H, m), 1.79 (3H, m), 2.71 (1H, m), 4.31 (2H, t), 7.20 (2H, d, J=14.1 Hz), 8.45 (2H, d, J=14.1 Hz), 8.71 (2H, s).

MS (m/e): 456 (M+).

This compound melted at 60.7° C. to give an isotropic liquid phase.

EXAMPLE 4

Synthesis of 2-(4-(S)-2,6-dimethylheptanoyloxyphenyl)-5-heptyloxycarbonyloxy-1,3-pyrimidine:

Synthesis was performed in the same manner as the one of Example 2 but using heptyl chloroformate as a substitute for the decyl chloroformate employed in Example 1 (1).

1H-NMR (CDCl$_3$) ppm: 0.90 (9H, m), 1.30 (11H, m), 1.42 (4H, m), 1.56 (2H, m), 1.78 (3H, m), 2.71 (1H, m), 4.32 (2H, t), 7.19 (2H, d, J=9.0 Hz), 8.45 (2H, d, J=8.9 Hz), 8.71 (2H, s).

MS (m/e): 470 (M+).

This compound melted at 73.8° C. to give an isotropic liquid phase.

EXAMPLE 5

Synthesis of 2-(4-(S)-2,6-dimethylheptanoyloxyphenyl)-5-octyloxycarbonyloxy-1,3-pyrimidine:

Synthesis was performed in the same manner as the one of Example 2 but using octyl chloroformate as a substitute for the decyl chloroformate employed in Example 1 (1).

1H-NMR (CDCl$_3$) ppm: 0.89 (9H, m), 1.29 (13H, m), 1.43 (4H, m), 1.56 (2H, m), 1.79 (3H, m), 2.71 (1H, m), 4.31 (2H, t), 7.20 (2H, d, J=9.0 Hz), 8.45 (2H, d, J=8.9 Hz), 8.71 (2H, s).

MS (m/e): 485 (M+).

This compound melted at 72.9° C. to give an isotropic liquid phase. When cooled quickly, a tiled smectic liquid crystal phase was observed immediately before crystallization. The results of a contact test of this compound with the compound of Example 1 indicated that the tilted smectic phases were the same, i.e., the antiferroelectric liquid crystal phase.

EXAMPLE 6

Synthesis of 2-(4-(S)-2,6-dimethylheptanoyloxyphenyl)-5-nonyloxycarbonyloxy-1,3-pyrimidine:

Synthesis was performed in the same manner as the one of Example 2 but using nonyl chloroformate as a substitute for the decyl chloroformate employed in Example 1 (1).

1H-NMR (CDCl$_3$) ppm: 0.89 (9H, m), 1.27 (15H, m), 1.42 (4H, m), 1.57 (2H, m), 1.77 (3H, m), 2.71 (1H, m), 4.31 (2H, t), 7.19 (2H, d, J=14.1 Hz), 8.45 (2H, d, J=14.1 Hz), 8.71 (2H, s).

MS (m/e): 499 (M++H).

This compound melted at 70.4° C. to give an isotropic liquid phase.

EXAMPLE 7

Synthesis of 2-(4-(S)-2,6-dimethylheptanoyloxyphenyl)-5-hexadecyloxycarbonyloxy-1,3-pyrimidine:

Synthesis was performed in the same manner as the one of Example 2 but using hexadecyl chloroformate as a substitute for the decyl chloroformate employed in Example 1 (1).

1H-NMR (CDCl$_3$) ppm: 0.89 (9H, m), 1.25 (26H, m), 1.31 (3H, d), 1.43 (4H, m), 1.56 (2H, m), 1.79 (3H, m), 2.71 (1H, m), 4.31 (2H, t), 7.20 (2H, d, J=8.9 Hz), 8.45 (2H, d, J=8.9 Hz), 8.71 (2H, s).

MS (m/e): 596 (M+).

This compound melted at 81.2° C. to give an isotropic liquid phase.

EXAMPLE 8

Synthesis of 2-(4-(S)-2-methylpentanoyloxyphenyl)-5-octyloxycarbonyloxy-1,3-pyrimidine:

Synthesis was performed in the same manner as the one of Example 1 but using octyl chloroformate and (S)-2-methylpentanoic acid as substitutes respectively for the decyl chloroformate employed in Example 1 (1) and the (S)-2-methyloctanoic acid employed in Example 1 (3).

1H-NMR (CDCl$_3$) ppm: 0.90 (3H, t), 0.98 (3H, t), 1.38 (16H, m), 1.77 (3H, m), 2.72 (1H, m), 4.31 (2H, t), 7.19 (2H, d, J=11.2 Hz), 8.44 (2H, d, J=11.3 Hz), 8.721 (2H, s).

MS (m/e): 442 (M+).

This compound melted at 53.9° C. to give an isotropic liquid phase.

EXAMPLE 9

Synthesis of 2-(4-(S)-2-methyldecanoyloxyphenyl)-5-octyloxycarbonyloxy-1,3-pyrimidine:

Synthesis was performed in the same manner as the one of Example 1 but using octyl chloroformate and (S)-2-methyldecanoic acid as substitutes respectively for the decyl chloroformate employed in Example 1 (1) and the (S)-2-methyloctanoic acid employed in Example 1 (3).

1H-NMR (CDCl$_3$) ppm: 0.88 (3H, t), 0.90 (3H, t), 1.34 (25H, m), 1.51 (1H, m), 1.78 (3H, m), 2.71 (1H, m), 4.32 (2H, t), 7.20 (2H, d, J=8.9 Hz), 8.45 (2H, d, J=8.9 Hz), 8.72 (2H, s).

MS (m/e): 513 (M+ +H).

This compound melted at 47.7° C. to give an isotropic liquid phase. When cooled quickly, a tilted smectic liquid crystal phase was observed immediately before crystallization.

EXAMPLE 10

An antiferroelectric liquid crystal composition can be obtained by mixing the compounds of the present invention.

Now, the composition of the antiferroelectric liquid crystal composition and its phase transition points will be shown.

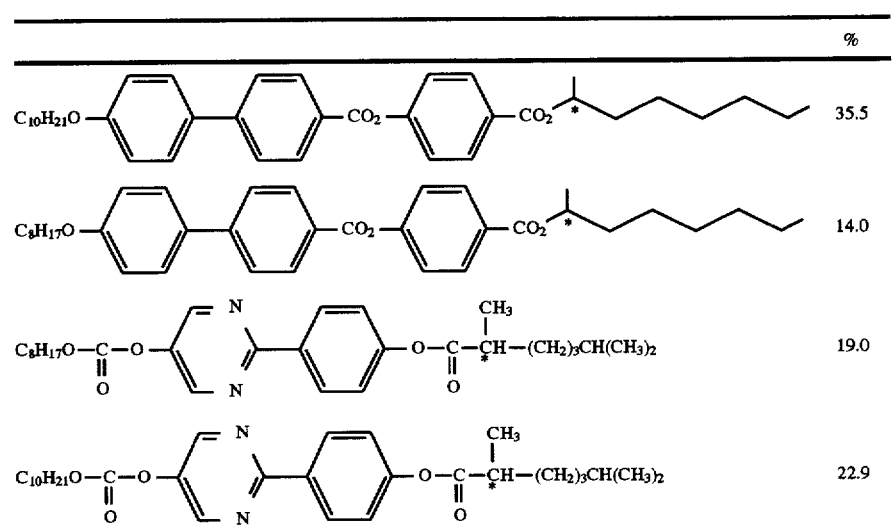

| | % |
|---|---|
| $C_8H_{17}O-\underset{O}{\underset{\|}{C}}-O-\text{[pyrimidine]}-\text{[phenyl]}-O-\underset{O}{\underset{\|}{C}}-\overset{CH_3}{\underset{*}{C}H}-(CH_2)_2CH_3$ | 8.6 |

This composition melted at 14° C. to give an antiferroelectric liquid crystal phase. It underwent transition into smectic A phase at 54° C. and to an isotropic liquid phase at 64° C.

As described above, a melting point depression is observed simply by mixing compounds, which are relatively similar to each other in structure, and a stable antiferroelectric liquid crystal phase appears. Thus the temperature range of the antiferroelectric liquid crystal phase can be broadened toward the lower temperature side.

EXAMPLE 11

An antiferroelectric liquid crystal composition can be obtained by mixing the compounds of the present invention with known compounds showing an antiferroelectric liquid crystal phase or a composition thereof in an ordinary manner. Now, the composition of the antiferroelectric liquid crystal composition and its phase transition points will be shown.

Namely, it began to melt at 10° C. to give an antiferroelectric liquid crystal phase. It underwent transition into a smectic A phase at 54.6° C. and to an isotropic liquid phase at 60° C.

As described above, the compounds of the present invention are highly miscible with known compounds showing an antiferroelectric liquid crystal phase or a composition thereof. Thus an antiferroelectric liquid crystal composition can be easily obtained.

EXAMPLE 12

An antiferroelectric liquid crystal composition can be obtained also by mixing the compounds of the present invention with known and optically inactive compounds showing a smectic C liquid crystal phase or a composition thereof. However, it is to be noted that the content of the compounds showing a smectic C liquid crystal phase or a composition thereof should be restricted to 40% at the largest.

| | % |
|---|---|
| $C_{10}H_{21}O-\text{[biphenyl]}-CO_2-\text{[phenyl]}-CO_2^*-\text{CH(C}_6\text{H}_{13})$ chain | 25.6 |
| $C_8H_{17}O-\text{[biphenyl]}-CO_2-\text{[phenyl]}-CO_2^*-\text{CH(C}_6\text{H}_{13})$ chain | 11.2 |
| $C_8H_{17}O-\text{[F-phenyl]}-\text{[phenyl]}-CO_2-\text{[F-phenyl]}-O-\underset{O}{\underset{\|}{C}}-\overset{CH_3}{\underset{*}{C}H}-(CH_2)_3CH(CH_3)_2$ | 6.1 |
| $C_8H_{17}O-\underset{O}{\underset{\|}{C}}-O-\text{[pyrimidine]}-\text{[phenyl]}-O-\underset{O}{\underset{\|}{C}}-\overset{CH_3}{\underset{*}{C}H}-(CH_2)_3CH(CH_3)_2$ | 27.6 |
| $C_{10}H_{21}O-\underset{O}{\underset{\|}{C}}-O-\text{[pyrimidine]}-\text{[phenyl]}-O-\underset{O}{\underset{\|}{C}}-\overset{CH_3}{\underset{*}{C}H}-(CH_2)_3CH(CH_3)_2$ | 13.7 |
| $C_8H_{17}O-\underset{O}{\underset{\|}{C}}-O-\text{[pyrimidine]}-\text{[phenyl]}-O-\underset{O}{\underset{\|}{C}}-\overset{CH_3}{\underset{*}{C}H}-(CH_2)_2CH_3$ | 15.8 |

The phase transition points of this composition were as follows.

Now, the composition of the antiferroelectric liquid crystal composition and its phase transition points will be shown.

| | % |
|---|---|
| C₈H₁₇O—C(=O)—O—[pyrimidine]—[phenyl]—O—C(=O)—C*H(CH₃)—(CH₂)₃CH(CH₃)₂ | 40.0 |
| C₁₀H₂₁O—C(=O)—O—[pyrimidine]—[phenyl]—O—C(=O)—C*H(CH₃)—(CH₂)₃CH(CH₃)₂ | 27.5 |
| C₈H₁₇O—[pyrimidine]—[phenyl]—OC₈H₁₇ | 9.4 |
| C₈H₁₇—[pyrimidine]—[phenyl]—OC₆H₁₃ | 23.1 |

This composition showed the following phase transition points.

Namely, it began to melt at 39° C. to give an antiferroelectric liquid crystal phase. It underwent transition into an isotropic liquid phase at 49° C.

As described above, the compounds of the present invention are highly miscible with known and optically inactive compounds showing a smectic C liquid crystal phase or a composition thereof. Thus an antiferroelectric liquid crystal composition can be easily obtained.

It is also possible to prepare an antiferroelectric liquid crystal composition by mixing the compounds of the present invention with compounds showing a chiral smectic C liquid crystal phase or a composition thereof, so long as these components are added in equivalent amounts.

COMPARATIVE EXAMPLE 1

No antiferroelectric liquid crystal phase could be obtained by adding more than 40% of a phenylpyrimidine compound, which simply showed a smectic C phase, to MHPDBC as shown in Example 1. For example, the following two-component system showed only a smectic A phase.

no tilted phase (for example, ferroelectric liquid crystal phase, antiferroelectric liquid crystal phase) appeared until local crystallization occurred at room temperature.

COMPARATIVE EXAMPLE 2

Similar to Comparative Example 1, a phenylpyrimidine compound, which showed simply a smectic C phase and had a high thermal stability of the liquid crystal phase, was added in an amount of more than 40% to MHPDBC as shown in Example 1. However, no antiferroelectric liquid crystal phase could be obtained thereby. For example, the following two-component system showed only a smectic A phase alone.

| | % |
|---|---|
| C₁₀H₂₁O—[phenyl]—[phenyl]—CO₂—[phenyl]—CO₂—*CH(CH₃)—C₆H₁₃ | 49.4 |
| C₈H₁₇—[pyrimidine]—[phenyl]—OC₆H₁₃ | 50.6 |

This mixture showed a smectic A phase and changed to an isotropic phase at 101° C. At lower temperatures, however,

| | % |
|---|---|
| $C_{10}H_{21}O$—⟨⟩—⟨⟩—$CO_2$—⟨⟩—$CO_2$—*—∼∼∼ | 48.7 |
| $C_8H_{17}O$—⟨N=N⟩—⟨⟩—$OC_8H_{17}$ | 51.3 |

This mixture also showed a smectic A phase and changed to an isotropic phase at 120° C. At lower temperatures, however, no tilted phase (for example, ferroelectric liquid crystal phase, antiferroelectric liquid crystal phase) appeared until local crystallization occurred at room temperature.

COMPARATIVE EXAMPLE 3

A phenylpyrimidine compound, which showed simply a smectic C phase and had an ester bond similar to the general formula (I), was added in an amount of more than 40% to MHPDBC as shown in Example 1. However, no antiferroelectric liquid crystal phase could be obtained thereby. For example, the following two-component system showed only a smectic A phase alone.

| | % |
|---|---|
| $C_{10}H_{21}O$—⟨⟩—⟨⟩—$CO_2$—⟨⟩—$CO_2$—*—∼∼∼ | 50.3 |
| $C_{10}H_{21}O$—⟨N=N⟩—⟨⟩—O—C(=O)—$C_9H_{19}$ | 49.7 |

This mixture also showed a smectic A phase and changed to an isotropic phase at 97.6° C. At lower temperatures, however, no tilted phase (for example, ferroelectric liquid crystal phase, antiferroelectric liquid crystal phase) appeared until local crystallization occurred at room temperature.

COMPARATIVE EXAMPLE 4

A phenylpyrimidine compound, which showed simply a smectic C phase and had an ester bond, was added in an amount of more than 40% to MHPDBC as shown in Example 1. However, no antiferroelectric liquid crystal phase could be obtained thereby. For example, the following two-component system showed only a smectic A phase and a ferroelectric liquid crystal phase.

| | % |
|---|---|
| $C_{10}H_{21}O$—⟨⟩—⟨⟩—$CO_2$—⟨⟩—$CO_2$—*—∼∼∼ | 48.7 |
| $C_{10}H_{21}O$—⟨N=N⟩—⟨⟩—$CO_2C_7H_{15}$ | 51.3 |

This mixture showed a chiral smectic C phase (ferroelectric phase) and changed to a smectic A phase at 84° C. and then changed to an isotropic phase at 105° C. At lower temperatures, however, no antiferroelectric liquid crystal phase appeared until local crystallization occurred at room temperature. This compound showed a stable ferroelectric liquid crystal phase seemingly due to the similarity to MHPDBC in the terminal ester bond. As described above, however, no antiferroelectric liquid crystal phase appeared.

COMPARATIVE EXAMPLE 5

A phenylpyrimidine compound, which showed simply a smectic C phase and had a high thermal stability of the liquid crystal phase similar to the one employed in Comparative Example 1, was added in an amount of more than 40% to MHPDBC as shown in Example 1. However, no antiferroelectric liquid crystal phase could be obtained thereby. For example, the following two-component system showed only a smectic A phase and a ferroelectric liquid crystal phase.

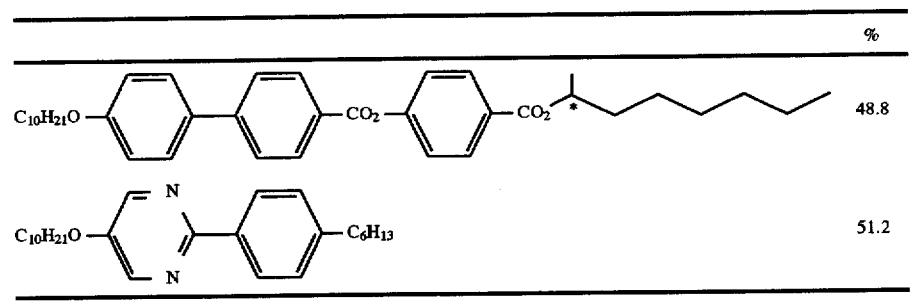

This mixture showed a chiral smectic C phase (ferroelectric phase) and changed to a smectic A phase at 38° C. and then changed to an isotropic phase at 102° C. At lower temperatures, however, no antiferroelectric liquid crystal phase appeared until local crystallization occurred at room temperature. Although this compound was similar in structure to the compounds employed in Comparative Examples 1 and 2, it showed the ferroelectric liquid crystal phase but no antiferroelectric liquid crystal phase.

COMPARATIVE EXAMPLE 6

A phenylpyrimidine compound, which had the same optically active group and ester bond as those in the general formula (I) of the present invention, was added in an amount of more than 40% to MHPDBC as shown in Example 1. However, no antiferroelectric liquid crystal phase could be obtained thereby. For example, the following two-component system showed only a smectic A phase alone.

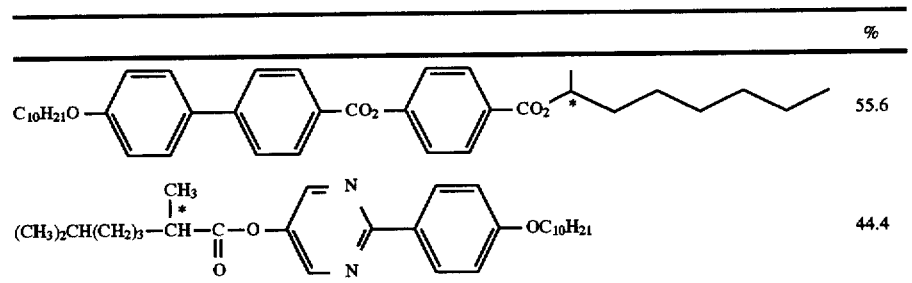

This mixture showed a chiral smectic A phase and changed to an isotropic phase at 80° C. At lower temperatures, however, no tilted phase (for example, ferroelectric liquid crystal phase, antiferroelectric liquid crystal phase) appeared until local crystallization occurred at room temperature.

As the above Comparative Examples 1 to 6 show, no antiferroelectric liquid crystal phase appears merely by adding more than 40% by weight of a compound, which is employed in a ferroelectric chiral smectic phase in general, to a compound showing an antiferroelectric liquid crystal phase such as MHPDBC. This is seemingly because a compound showing an antiferroelectric liquid crystal phase differs from a compound employed in a ferroelectric chiral smectic phase in the layer structure of the tilted smectic phase thus presented.

COMPARATIVE EXAMPLE 7

Synthesis of 2-(4-heptanoyloxyphenyl)-5-octyloxycarbonyloxy-1,3-pyrimidine:

Synthesis was performed in the same manner as the one of Example 1 but using n-heptanoic acid as a substitute for the (S)-2-methyloctanoic acid employed in Example 1 (3).

1H-NMR (CDCl$_3$) ppm: 0.90 (6H, m), 1.33 (16H, m), 1.77 (4H, m), 2.53 (2H, t), 4.32 (2H, t), 7.21 (2H, d, J=9.0 Hz), 8.45 (2H, d, J=9.0 Hz), 8.71 (2H, s).

MS (m/e): 457 (M+, +H).

Although this compound is disclosed in JP-A-4-213387, this reference states nothing about its phase transition points. Thus it was synthesized as described above and the phase transition temperature thereof was examined. As a result, it melted and showed a smectic C phase at 59.8° C., changed to a nematic phase at 74.5° C. and then changed to an isotropic phase at 75.5° C. Accordingly, this compound had a higher thermal stability as the whole liquid crystal phase than the compound of the present invention represented by the general formula (I).

Then it was added in an amount of 49.3% by weight to MHPDBC, i.e., a compound showing an antiferroelectric liquid crystal phase, as done in Comparative Examples 1 to 6. Then the phase transition temperature of the composition thus obtained was examined. As a result, it showed a liquid crystal phase and changed to a smectic A phase at 60° C. and then changed to an isotropic phase at 101° C. In the process of cooling, it showed the smectic A phase alone until crystallization occurred at around 40° C.

That is to say, no stable antiferroelectric liquid crystal phase can be obtained by adding a compound, which is similar in structure to the general formula (I) of the present invention but merely has carbonate, alkanate and a phenylpyrimidine structure, to an antiferroelectric liquid crystal composition.

These Examples and Comparative Examples indicate that the compound of the present invention represented by the general formula (I), which is specified by carbonate, optically active 2-methylalkanate, the direction of the phenylpyrimidine ring, etc., is one being capable of presenting a stable antiferroelectric liquid crystal phase on mixing.

The optically active compound of the present invention is highly miscible with a number of known antiferroelectric liquid crystal compounds. Therefore it is capable of providing liquid crystal materials having improved temperature characteristics. Further, the liquid crystal composition containing the optically active compound of the present invention is usable in electro-optical devices with the use of antiferroelectric liquid crystals.

While the invention has been described in detail and with reference to specific embodiments thereof, it will be apparent to one skilled in the art that various changes and modifications can be made therein without departing from the spirit and scope thereof.

What is claimed is:

1. An antiferroelectric liquid crystal compound represented by the following general formula (I):

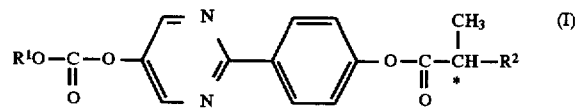

wherein $R^1$ represents an alkyl group having 6 to 16 carbon atoms; $R^2$ represents a straight chain alkyl group having 3 to 8 carbon atoms or a branched alkyl group having 4 to 10 carbon atoms; and * means an asymmetric carbon atom.

2. The antiferroelectric liquid crystal compound as claimed in claim 1, wherein $R^1$ is a straight chain alkyl group having 6 to 12 carbon atoms.

3. The antiferroelectric liquid crystal compound as claimed in claim 1, wherein $R^1$ is a straight chain or branched alkyl group having 3 to 6 carbon atoms in the linear chain.

4. An antiferroelectric liquid crystal composition comprising at least one antiferroelectric liquid crystal compound represented by the following general formula (I):

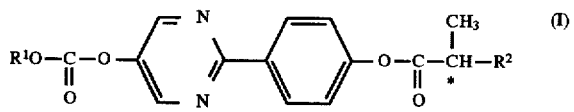

wherein $R^1$ represents an alkyl group having 6 to 16 carbon atoms; $R^2$ represents a straight chain alkyl group having 3 to 8 carbon atoms or a branched alkyl group having 4 to 10 carbon atoms; and * means an asymmetric carbon atom.

5. The antiferroelectric liquid crystal composition as claimed in claim 4, wherein $R^1$ is a straight chain alkyl group having 6 to 12 carbon atoms.

6. The antiferroelectric liquid crystal composition as claimed in claim 4, wherein $R^2$ is a straight chain or branched alkyl group having 3 to 6 carbon atoms in the linear chain.

7. The antiferroelectric liquid crystal composition as claimed in claim 4, wherein the antiferroelectric liquid crystal compound represented by general formula (I) is contained in an amount of 1 to 60% by weight.

8. The antiferroelectric liquid crystal composition as claimed in claim 4, wherein the antiferroelectric liquid crystal compound represented by general formula (I) is contained in an amount of 20 to 60% by weight.

* * * * *